US00PP33423P2

(12) United States Plant Patent
von Tubeuf

(10) Patent No.: US PP33,423 P2
(45) Date of Patent: Aug. 31, 2021

(54) POINSETTIA PLANT NAMED 'NPCW20049'

(50) Latin Name: *Euphorbia pulcherrima*
Varietal Denomination: NPCW20049

(71) Applicant: Klemm+Sohn GmbH & Co. KG, Stuttgart (DE)

(72) Inventor: Guido von Tubeuf, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 17/168,494

(22) Filed: Feb. 5, 2021

(51) Int. Cl.
*A01H 5/02* (2018.01)
*A01H 6/38* (2018.01)

(52) U.S. Cl.
USPC ..... Plt./307
CPC ..... *A01H 6/385* (2018.05)

(58) Field of Classification Search
USPC ..... Plt./307
CPC ..... A01H 6/385; A01H 6/38; A01H 5/02
See application file for complete search history.

*Primary Examiner* — Keith O. Robinson
(74) *Attorney, Agent, or Firm* — Weatherly IP Solutions, LLC; Barbara Campbell

(57) ABSTRACT

A new *Poinsettia* plant particularly distinguished by having red bracts, an upright habit, and having a triangular plant form, is disclosed.

1 Drawing Sheet

Genus and species: *Euphorbia pulcherrima.*
Variety denomination: 'NPCW20049'.

BACKGROUND OF THE NEW PLANT

The present invention comprises a new and distinct variety of *Poinsettia*, botanically known as *Euphorbia pulcherrima* and hereinafter referred to by the variety name 'NPCW20049'. 'NPCW20049' was derived from a cross conducted Nairobi, Kenya in December 2012 between the female *Poinsettia* 'NPCW12200', also known as CHRISTMAS 'Glory Red' (U.S. Plant Pat. No. 25,049) and the male *Poinsettia* 'NPCW02044', also known as CHRISTMAS 'Feelings Red' (U.S. Plant Pat. No. 14,618).

Seedlings from the cross were subsequently planted and in October 2013, a single plant was selected in Stuttgart, Germany. In April 2014, 'NPCW20049' was first asexually propagated by vegetative apical cuttings in Stuttgart, Germany. 'NPCW20049' was found to reproduce true to type in successive generations of asexual propagation via vegetative apical cuttings in Stuttgart, Germany.

SUMMARY

The following are the most outstanding and distinguishing characteristics of this new variety when grown under normal horticultural practices in Stuttgart, Germany.

1. Red bracts; and
2. Having a triangular plant form and an upright habit.

DESCRIPTION OF THE PHOTOGRAPH

This new *Poinsettia* plant is illustrated by the accompanying photograph which shows an overall view of the whole plant. The photograph is of a plant approximately 14-weeks-old grown indoors in Stuttgart, Germany in December 2016.

The colors shown are as true as can be reasonably obtained by conventional photographic procedures.

DESCRIPTION OF THE NEW VARIETY

The following detailed descriptions set forth the distinctive characteristics of 'NPCW20049'. The data which define these characteristics were collected from asexual reproductions carried out in Stuttgart, Germany. Data was collected on plants that were aged 19-weeks after potting and grown in a glass greenhouse under normal horticultural practices in Stuttgart, Germany in insert August to December 2020. Color references are to The R.H.S. Colour Chart of The Royal Horticultural Society of London (R.H.S.), 5$^{th}$ edition (2007) unless where otherwise stated.

Classification:
- *Family.*—Euphorbiaceae.
- *Species.—Euphorbia pulcherrima.*
- *Common name.—Poinsettia.*
- *Variety.*—'NPCW20049'.

Parentage:
- *Female.*—'NPCW12200', also known as CHRISTMAS 'Glory Red' (U.S. Plant Pat. No. 25,049).
- *Male.*—'NPCW02044', also known as CHRISTMAS 'Feelings Red' (U.S. Plant Pat. No. 14,618).

Plant:
- *Form.*—Triangular.
- *Growth habit.*—Upright.
- *Vigor.*—Very low.
- *Height.*—16 cm to 19 cm.
- *Width.*—28 cm to 31 cm.
- *Average number of inflorescences per plant.*—5 to 6.
- *Keeping quality.*—Very good.
- *Time to produce a cutting.*—4 weeks.
- *Flowering response time.*—Approximately 60 days.
- *Propagation type.*—Apical cuttings.
- *Rooting habit and root color.*—Freely branching and white.

Lateral branches:
*Color*.—RHS 137D.
*Length*.—14 cm to 18 cm.
*Internode length*.—0.4 cm to 2.0 cm.
*Diameter*.—0.4 cm to 0.7 cm.
*Branching habit*.—Freely branching.
*Number of lateral branches per plant*.—6 to 7.
*Texture*.—Smooth.
*Strength*.—Sturdy.

Leaves:
*Quantity*.—4 to 5 per lateral branch.
*Arrangement*.—Alternate.
*Number of lobes on the leaf blade*.—0 to 2.
*Lobation depth*.—Shallow to medium and some leaves do not have lobation.
*Depth of the deepest sinus of the leaf blade*.—1.0 cm.
*Shape*.—Obtuse.
*Apex*.—Acuminate.
*Base*.—Rounded.
*Margin*.—Mostly almost entire, but some are slightly serrate.
*Length*.—8.0 cm to 11.0 cm.
*Width*.—3.0 cm to 5.5 cm.
*Texture* (*both upper and lower surfaces*).—Smooth.
*Vein color*.—Upper surface: No color; transparent. Lower surface: Between RHS 139C and RHS 139D.
*Variegation*.—Absent.
*Venation pattern*.—Reticulate.
*Color*.—Mature foliage: Upper surface: Close to RHS 139A. Lower surface: RHS N138B. Immature foliage: Upper surface: RHS N137D. Lower surface: RHS 139C.
*Leaf petiole*.—Length: 2.0 cm to 3.5 cm. Diameter: 0.2 cm to 0.3 cm. Color: Upper (part) surface: RHS 59A (Red-Purple). Lower (part) surface: RHS 181B (Greyed-Red). Texture: Smooth. Strength: Medium.
*Transitional leaves*.—Few.

Inflorescence:
*Type and habit*.—Cluster of cyathia.
*Quantity per lateral branch*.—1.
*Position relative to foliar plane*.—Slightly below.
*Lastingness of inflorescence on the plant*.—4 to 5 weeks.
*Natural flowering season*.—Beginning of December.
*Diameter*.—17.0 cm to 20.0 cm.
*Height*.—2.5 cm to 3.0 cm.
*Fragrance*.—Absent.

Bracts:
*Number of bracts per inflorescence*.—6 plus 5 to 6 smaller ones in the inner circle.
*Shape*.—Obtuse.
*Apex*.—Acuminate.
*Base*.—Rounded.
*Margin*.—Slightly serrate.
*Size*.—Length: 3.0 cm to 8.0 cm. Width: 2.0 cm to 6.0 cm.
*Texture* (*both upper and lower surfaces*).—Smooth.
*Folding along the main vein*.—Absent.
*Twisting*.—Absent.
*Rugosity between the veins*.—Absent.
*Venation pattern*.—Reticulate.
*Vein color*.—Upper surface: RHS 59A. Lower surface: RHS 181A.
*Bract color*.—Upper surface: Close to RHS 46B. Lower surface: Close to RHS 45B.
*Bract petiole*.—Length: 0.4 cm to 1.0 cm. Diameter: 0.2 cm. Color: Upper (part) surface: RHS 59A. Lower (part) surface: RHS 181B. Texture: Smooth. Strength: Medium.

Cyme:
*Diameter*.—1.0 cm to 1.5 cm.
*Cyathia number*.—5 to 9 per inflorescence.
*Deformation of glands of the cyathium*.—Absent.
*Timing of opening of cyathia*.—Opens beginning of December; first pollen appears in parallel to opening of the nectar cups, stigmas arrive 2 to 3 weeks later.
*Cyathium*.—Shape: Ovate. Texture (inner and outer surfaces): Smooth. Diameter: 0.2 cm to 0.5 cm. Length: 0.3 cm to 0.7 cm. Color: RHS 143C.
*Peduncle*.—Color: RHS 142B. Length: 0.2 cm. Diameter: 0.1 cm. Texture: Smooth. Strength: Medium.
*Nectar cups*.—Number: 1 per cyathium. Diameter: 0.1 cm. Length: 0.3 cm to 0.4 cm. Color: RHS 12A. Shape: Lip-shaped. Texture (inner and outer surfaces): Smooth.

Reproductive organs:
*Stamen quantity*.—15 to 20 per cyathium.
*Stamen shape*.—Ovate.
*Filament length*.—0.25 cm.
*Filament color*.—RHS 46A.
*Pollen quantity*.—Moderate.
*Pollen color*.—RHS 12A.
*Gynoecium*.—Not observed.

Fruit and seed set: None observed.
Disease and pest resistance: None observed.

COMPARISON WITH PARENTAL AND COMMERCIAL LINES

When 'NPCW20049' is compared to its parental lines, the following differences are noted in Table 1.

TABLE 1

| Characteristic | 'NPCW20049' | 'NPCW12200' | 'NPCW02044' |
|---|---|---|---|
| Earliness to flower | Late | Early | Medium |
| Bract size | Small | Large | Medium |
| Vigor | Very low | Low | Medium |

When 'NPCW20049' is compared to the commercial line 'NPCW10158' (U.S. Plant Pat. No. 22,580, the following differences are noted in Table 2.

TABLE 2

| Characteristic | 'NPCW20049' | 'NPCW10158' |
|---|---|---|
| Plant height | 16.0 cm to 19.0 cm | 25.0 cm to 28.0 cm |
| Plant width | 28.0 cm to 31.0 cm | 20.0 cm to 30.0 cm |

I claim:

1. A new and distinct variety of *Poinsettia* plant designated 'NPCW20049' as illustrated and described herein.

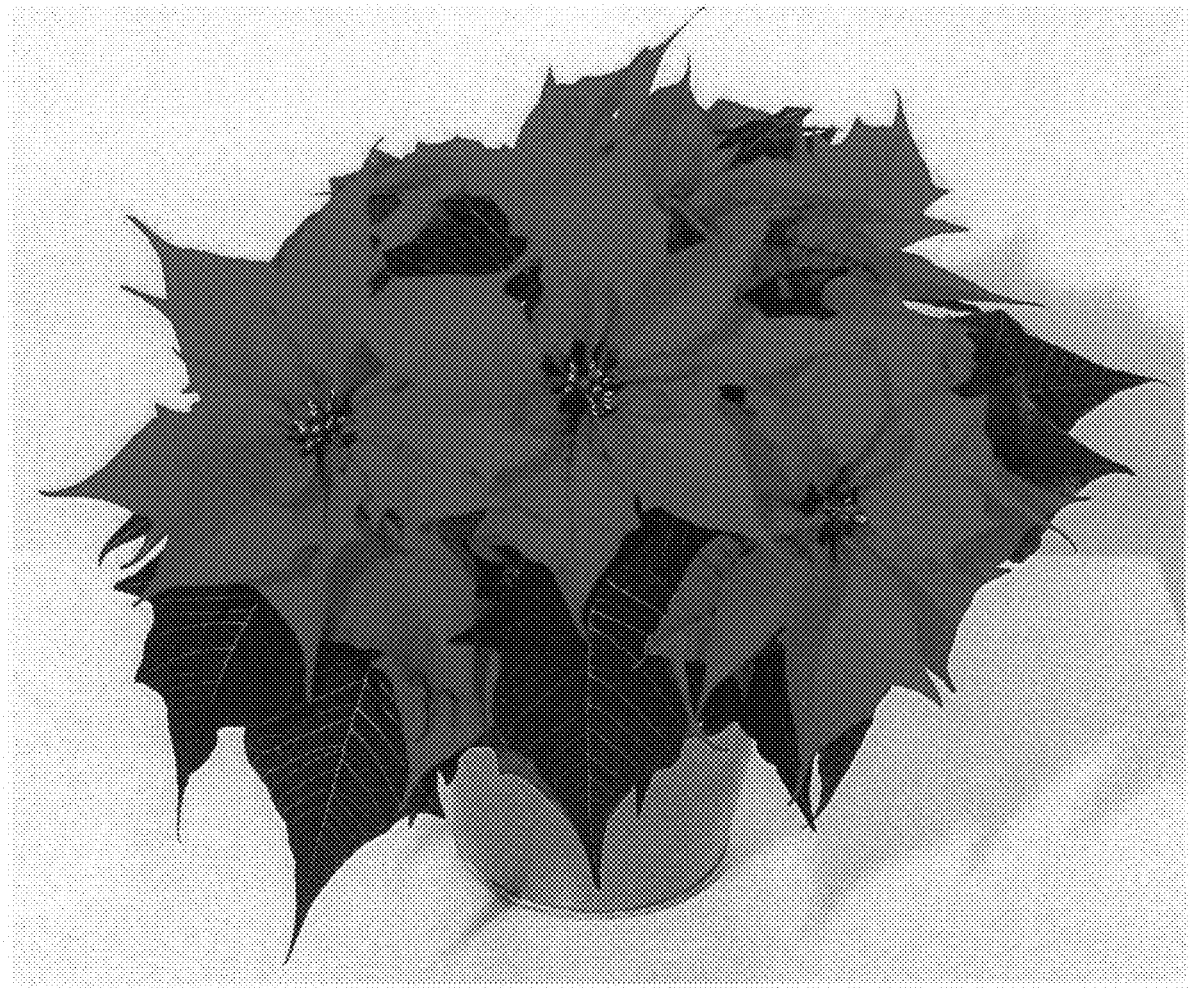

* * * * *